(12) United States Patent
Rauchwerger

(10) Patent No.: US 9,743,950 B2
(45) Date of Patent: Aug. 29, 2017

(54) WIRE-GUIDED SURGICAL INSTRUMENT

(71) Applicant: Jacob Jeffrey Rauchwerger, Cedarhurst, NY (US)

(72) Inventor: Jacob Jeffrey Rauchwerger, Cedarhurst, NY (US)

(73) Assignee: AMBITUS MEDICAL SUPPLIES LLC, Oceanside, NY (US)

(*) Notice: Subject to any disclaimer, the term of this patent is extended or adjusted under 35 U.S.C. 154(b) by 387 days.

(21) Appl. No.: 13/774,009

(22) Filed: Feb. 22, 2013

(65) Prior Publication Data

US 2013/0218183 A1   Aug. 22, 2013

Related U.S. Application Data

(60) Provisional application No. 61/601,701, filed on Feb. 22, 2012.

(51) Int. Cl.
*A61B 17/3211* (2006.01)
*A61B 17/22* (2006.01)

(52) U.S. Cl.
CPC . *A61B 17/3211* (2013.01); *A61B 2017/22039* (2013.01); *A61B 2017/32113* (2013.01)

(58) Field of Classification Search
CPC ............ A61B 17/32; A61B 17/320052; A61B 17/3205; A61B 17/3209; A61B 17/32093; A61B 17/3211; A61B 17/3403; A61B 17/0482; A61B 2017/32113; A61B 2017/22038; A61B 2017/22039; A61B 2017/22041; A61B 2017/3405
See application file for complete search history.

(56) References Cited

U.S. PATENT DOCUMENTS

| | | | |
|---|---|---|---|
| 3,754,693 A * | 8/1973 | Herr | 223/102 |
| 5,250,063 A | 10/1993 | Abidin et al. | |
| 5,599,351 A * | 2/1997 | Haber | A61B 17/3211 30/151 |
| 7,341,596 B2 | 3/2008 | Heppler | |
| 8,016,845 B1* | 9/2011 | Sauer | 606/170 |
| 8,925,443 B2 | 1/2015 | Agarwal et al. | |
| 2004/0181246 A1 | 9/2004 | Heppler | |
| 2005/0177183 A1 | 8/2005 | Thorne et al. | |
| 2005/0240165 A1 | 10/2005 | Miki et al. | |

(Continued)

FOREIGN PATENT DOCUMENTS

| | | |
|---|---|---|
| CN | 202776486 U | 3/2013 |
| EP | 2 138 200 | 12/2009 |
| EP | 2 311 394 A1 | 4/2011 |

(Continued)

OTHER PUBLICATIONS

International Search Report and Written Opinion of the International Searching Authority dated Jun. 13, 2013, from corresponding International Application No. PCT/US2013/027272.

(Continued)

*Primary Examiner* — Todd J Scherbel
(74) *Attorney, Agent, or Firm* — Katten Muchin Rosenman LLP

(57) ABSTRACT

Disclosed herein is a surgical instrument having a cylindrical tube affixed thereto. The axis of the cylindrical tube is aligned with a central axis of the surgical instrument so it can be advanced along a guidewire.

7 Claims, 3 Drawing Sheets

(56) References Cited

U.S. PATENT DOCUMENTS

2008/0077146 A1    3/2008   Pernsteiner et al.
2012/0226299 A1    9/2012   Heppler

FOREIGN PATENT DOCUMENTS

| JP | 2008-67810 | 3/2008 |
|----|------------|--------|
| WO | 93/25152 | 12/1993 |
| WO | 93/25152 A1 | 12/1993 |
| WO | 2012/044633 A1 | 4/2012 |
| WO | 2013/126661 A1 | 8/2013 |

OTHER PUBLICATIONS

International Search Report and Written Opinion dated Nov. 20, 2014, from PCT/US2014/049913.
Supplementary European Search Report dated Nov. 28, 2016, from the corresponding EP Application No. 14835391.5.

* cited by examiner

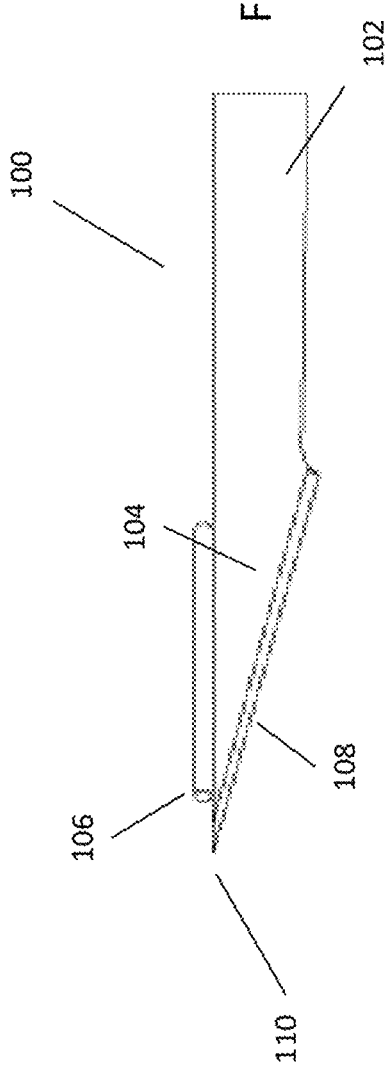
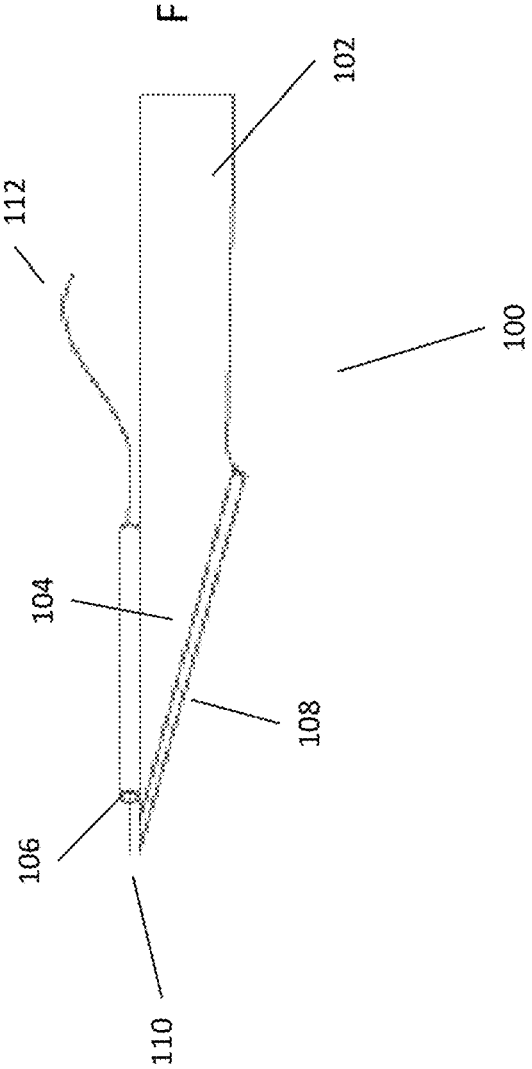

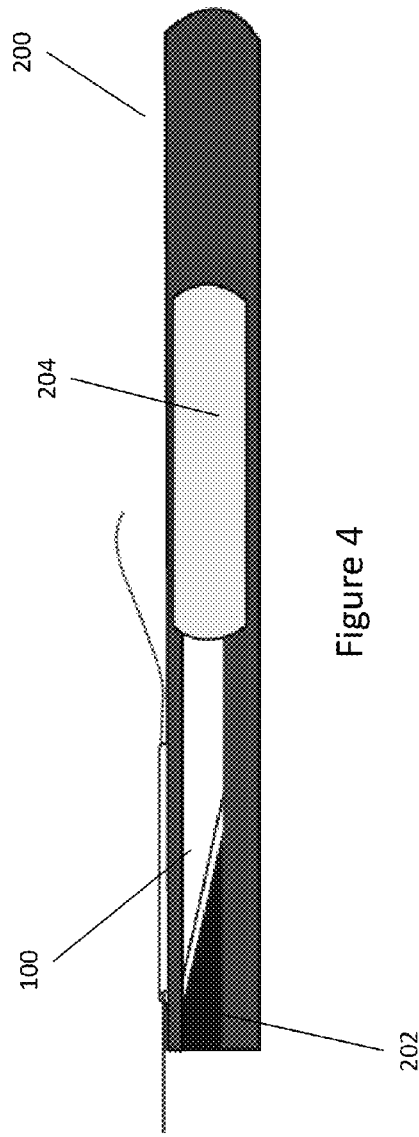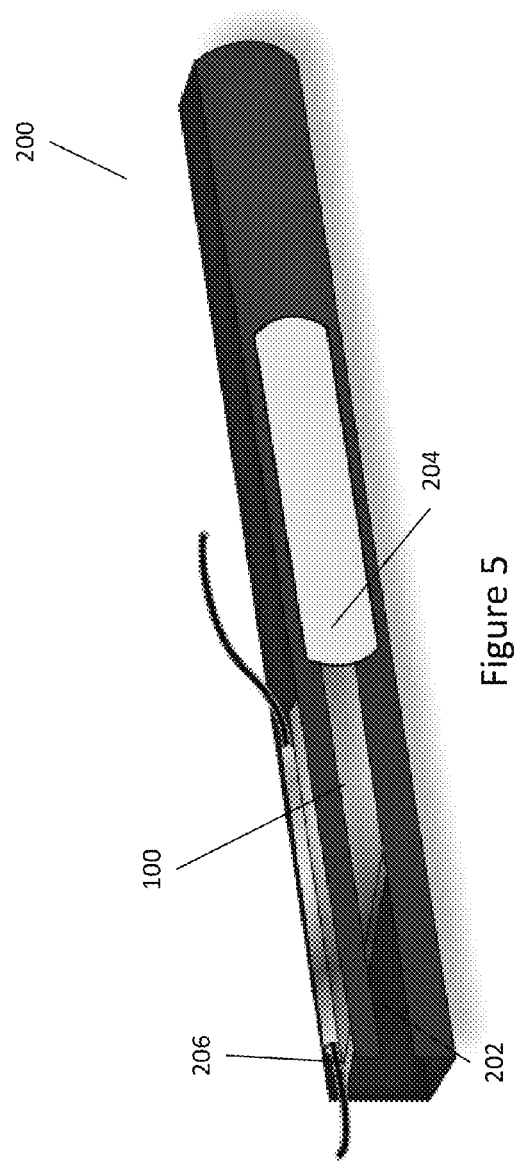

WIRE-GUIDED SURGICAL INSTRUMENT

CROSS REFERENCE TO RELATED APPLICATIONS

The present application claims priority to U.S. Provisional Application No. 61/601,701, filed Feb. 22, 2012, the entire content of which is incorporated by reference in its entirety.

FIELD OF THE INVENTION

The invention is directed to a surgical instrument having a cylindrical tube for accommodating a guidewire therein.

BACKGROUND OF THE INVENTION

Surgical instruments, such as scalpels, are used to make an incision in the skin, enabling insertion of devices whose purpose is to deliver various substances to the body. In order to minimize the size of the incision, a guidewire is inserted into the body cavity and instruments can be reliably advanced over the guidewire and into the body cavity for proper placement. This method is known as the "Seldinger Technique." In many circumstances, the guidewire incision needs to be widened in order to accommodate larger medical devices such as a trocar or catheter. The enlargement is typically done by hand which may lead to an imprecise or larger than needed cut. Therefore, a need clearly exists for a surgical instrument capable of using the guidewire to aid a surgical device, such as a scalpel, in making a more precise incision

SUMMARY OF THE INVENTION

The present invention provides a surgical instrument with a cylindrical tube affixed thereto. Preferably, the cylindrical tube is affixed to a top edge of the surgical instrument. However, the cylindrical tube may be affixed to any side (e.g., side or bottom) depending upon the intended use of the surgical instrument.

The cylindrical tube is affixed close to the tip of the surgical instrument to minimize the distance between the tip of the surgical instrument and the edge and the guidewire. This allows a user, for example, to minimize the size of an incision and to eliminate the potential for inadvertent skin nicks. In some embodiments, the surgical instrument can also be housed in a sheath.

BRIEF DESCRIPTION OF THE DRAWINGS

FIG. 1 is a view of the surgical instrument having a cylindrical tube attached thereto.

FIG. 2 is a view of the surgical instrument of FIG. 1 with a guidewire inserted through the cylindrical tube.

FIGS. 3-5 are views of an alternate embodiment of the surgical instrument encased in a sheath.

DETAILED DESCRIPTION OF THE INVENTION

Figure 3:
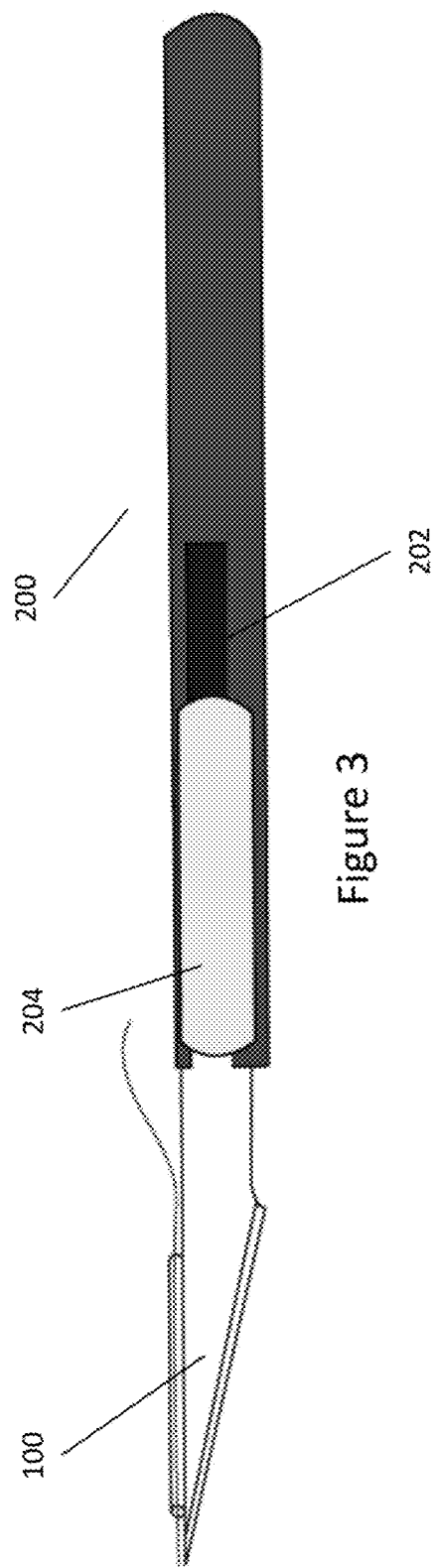

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

With reference to FIG. 1, depicted in surgical instrument 100 having proximal end 102 and distal end 104. Distal end 104 has cylindrical tube 106 affixed to the edge of the surgical instrument 100 for accommodating a guidewire. As shown, cylindrical tube 106 is affixed to the top edge of the surgical instrument 100. However, cylindrical tube 106 may be affixed to any side (e.g., sides or bottom) depending upon the intended use of surgical instrument 100. Proximal end 102 preferably comprises a handle to allow a user to operate surgical device 100.

In a preferred embodiment, surgical instrument 100 is a scalpel having cutting edge 108 for cutting a skin surface. Cutting edge 108 may comprise a cap or cover in order to protect a user and prevent cutting edge 108 from dulling. Cylindrical tube 106 is affixed close to tip 110 of surgical instrument 100 to minimize the distance between tip 110 and the edge and a guidewire inserted through cylindrical tube 106.

To use surgical instrument 100, guidewire 112 is threaded through cylindrical tube 106 as depicted in FIG. 2. Surgical instrument 100 can then be advanced over guidewire 112 to a skin surface (not shown). An incision can then be made using cutting edge 108. The incision is precise because cylindrical tube 106 limits the range of movement of surgical instrument 100, thereby avoiding any inadvertent skin nicks to the skin surface. Additionally, the cylindrical tube 106 allows for precise movement of surgical instrument 100, thereby eliminating residual skin tags after incision that may prevent smooth advancement of catheters or devices over the guidewire 112.

An alternate embodiment of surgical instrument 100 is depicted in FIGS. 3-5. As shown, surgical instrument 100 can be encased in sheath 200. Sheath 200 has a first channel 202 for accommodating the connection between button 204 and surgical instrument 100. Button 204 is used to move surgical instrument 100 from a closed position (FIG. 4) to an open position (FIG. 3). In some embodiments, the surgical instrument is maintained in the open and/or closed position by a locking mechanism, similar to that of a utility knife. Sheath 200 further comprises a second channel 206 for accommodating cylindrical tube 106 when surgical instrument 100 is in a closed position.

Sheath 200 protects an operator from lacerations while threading guidewire 106 through cylindrical tube 106. For example, during threading, surgical instrument 100 remains in a closed position (FIG. 4). Surgical instrument 100 can then be advanced to an open position (FIG. 3) when surgical instrument 100 is close to the desired incision location.

While the present invention has been described at some length and with some particularity with respect to the several described embodiments, it is not intended that it should be limited to any such particulars or embodiments or any particular embodiment, but it is to be construed to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A surgical instrument for advancement over a preinserted guidewire as used during performance of the Seldinger or modified Seldinger techniques, the surgical instrument comprising:
   a rigid body having a proximal end, a distal end, a top edge, a bottom edge, a left side, and a right side,
   wherein the top edge is opposite the bottom edge, and wherein the left side is opposite the right side;
   a blade having a cutting edge formed at the distal end of the body along the bottom edge of the body extending to a tip of the body, the cutting edge extending a length from the bottom edge of the body to the tip at a fixed angle,
   wherein the tip of the rigid body and a tip of the blade end in close proximity to one another; and
   a closed rigid cylindrical tube immovably affixed to only the top edge of the body at the distal end of the body in close proximity to the tip of the body,
   wherein the closed rigid cylindrical tube is configured to be threaded over the preinserted guidewire by inserting the preinserted guidewire into a proximal end of the closed rigid cylindrical tube near the tip of the blade and the surgical instrument is advanced over the preinserted guidewire to a skin surface to perform a dermototomy incision during the Seldinger or modified Seldinger techniques using the cutting edge of the blade,
   wherein the tip of the blade extends past a proximal end and a distal end of the closed rigid cylindrical tube,
   wherein the rigid body is configured to be encased within a scalpel sheath such that the rigid body is movable relative to the scalpel sheath between a closed position retracted within the scalpel sheath to an open position at least partially advanced relative to the scalpel sheath.

2. The surgical instrument of claim 1, wherein a central axis of the surgical instrument, a central axis of the cylindrical tube, and a central axis of the blade are coplanar.

3. The surgical instrument of claim 1, wherein the proximal end of the body comprises a handle.

4. The surgical instrument of claim 1, further comprising: the sheath surrounding the surgical instrument.

5. The surgical instrument of claim 4, wherein the sheath comprises a first channel for accommodating a button attached to the surgical instrument.

6. The surgical instrument of claim 5, wherein the button is used to move the surgical instrument from the closed position to the open position.

7. The surgical instrument of claim 6, wherein the sheath further comprises a second channel for accommodating the cylindrical tube when the surgical instrument is in the closed position.

* * * * *